United States Patent
Nason et al.

(10) Patent No.: US 11,224,417 B2
(45) Date of Patent: Jan. 18, 2022

(54) DEVICES AND METHODS FOR KNOTLESS MATERIAL FIXATION

(71) Applicant: CAYENNE MEDICAL, INC., Scottsdale, AZ (US)

(72) Inventors: Kevin S. Nason, Chandler, AZ (US); Derek J. Harper, Scottsdale, AZ (US); Kevin N. Baird, Scottsdale, AZ (US); James C. Dreese, Scottsdale, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 212 days.

(21) Appl. No.: 16/025,754

(22) Filed: Jul. 2, 2018

(65) Prior Publication Data

US 2018/0310930 A1    Nov. 1, 2018

Related U.S. Application Data

(62) Division of application No. 14/450,110, filed on Aug. 1, 2014, now Pat. No. 10,034,663.
(Continued)

(51) Int. Cl.
*A61B 17/04* (2006.01)
*A61B 90/90* (2016.01)

(52) U.S. Cl.
CPC .......... *A61B 17/0401* (2013.01); *A61B 90/90* (2016.02); *A61B 2017/044* (2013.01);
(Continued)

(58) Field of Classification Search
CPC ........ A61B 17/0401; A61B 2017/0414; A61B 2017/044; A61B 2017/0445;
(Continued)

(56) References Cited

U.S. PATENT DOCUMENTS 5,904,704 A * 5/1999 Goble ................ A61B 17/0401
                                                          606/232
5,980,558 A * 11/1999 Wiley ................ A61B 17/0401
                                                          606/104
(Continued)

OTHER PUBLICATIONS

"U.S. Appl. No. 14/450,110, Final Office Action dated Nov. 3, 2016", 12 pgs.
(Continued)

*Primary Examiner* — Katherine M Shi
(74) *Attorney, Agent, or Firm* — Schwegman Lundberg & Woessner, P.A.

(57) ABSTRACT

A simple, threaded suture anchor is pre-loaded with suture in a configuration that allows a surgeon to compress tissue against the bone without tying a knot. The knot-tying step is replaced by a simple suture looping step which requires less time and is not prone to errors in knot tying technique. The suture anchor is a screw-in style anchor body. The suture is loaded into the anchor in a configuration that allows it to create a loop on top of the tissue after it has been passed through the tissue from bottom to top. The suture limbs are then loaded into a knotless anchor which is implanted off the lateral edge of the tissue. Tensioning of the suture limbs in the knotless anchor tightens the loop on top of the tissue, providing a fulcrum point of fixation over the pre-loaded suture anchor without the otherwise need for requisite knot tying.

15 Claims, 13 Drawing Sheets

Related U.S. Application Data (60) Provisional application No. 61/861,274, filed on Aug. 1, 2013.

(52) U.S. Cl.
CPC ............... *A61B 2017/0446* (2013.01); *A61B 2017/0475* (2013.01); *A61B 2017/0496* (2013.01)

(58) Field of Classification Search
CPC .... A61B 2017/0464; A61B 2017/0458; A61B 2017/0412; A61B 2017/0427; A61B 2017/0448; A61B 2017/0453; A61B 2017/0403; A61B 2017/045; A61B 2017/0475; A61B 2017/0446; A61B 2017/0425; A61B 2017/0406; A61F 2/0811; A61F 2002/0858; A61F 2002/0888; A61F 2002/0817

See application file for complete search history.

(56) References Cited

U.S. PATENT DOCUMENTS

| | | | |
|---|---|---|---|
| 7,585,311 B2 | 9/2009 | Green et al. | |
| 8,062,334 B2 | 11/2011 | Green et al. | |
| 8,100,942 B1 | 1/2012 | Green et al. | |
| 8,109,969 B1 | 2/2012 | Green et al. | |
| 8,267,964 B2 | 9/2012 | Green et al. | |
| 10,034,663 B1 | 7/2018 | Nason et al. | |
| 2006/0079904 A1* | 4/2006 | Thal ................... | A61B 17/0401 606/232 |
| 2006/0282081 A1 | 12/2006 | Fanton et al. | |
| 2007/0060922 A1* | 3/2007 | Dreyfuss ............ | A61B 17/0401 606/326 |
| 2009/0082805 A1 | 3/2009 | Kaiser et al. | |
| 2010/0292732 A1* | 11/2010 | Hiratsuka ............... | B29C 45/00 606/232 |
| 2011/0224727 A1* | 9/2011 | Housman ............. | A61B 17/861 606/232 |
| 2011/0264138 A1 | 10/2011 | Avelar et al. | |
| 2012/0165866 A1 | 6/2012 | Kaiser et al. | |
| 2012/0179199 A1 | 7/2012 | Hernandez et al. | |
| 2013/0110165 A1 | 5/2013 | Burkhart et al. | |
| 2014/0188165 A1 | 7/2014 | Sengun et al. | |
| 2014/0364906 A1* | 12/2014 | Palese ................ | A61B 17/0401 606/232 |

OTHER PUBLICATIONS

"U.S. Appl. No. 14/450,110, Non Final Office Action dated Jul. 18, 2016", 11 pgs.

"U.S. Appl. No. 14/450,110, Notice of Allowance dated Mar. 28, 2018", 9 pgs.

"U.S. Appl. No. 14/450,110, Response filed Aug. 4, 2017 to Final Office Action dated Nov. 3, 2016", 12 pgs.

"U.S. Appl. No. 14/450,110, Response filed Oct. 18, 2016 to Non Final Office Action dated Jul. 18, 2016", 10 pgs.

"U.S. Appl. No. 14/450,110, Response filed Jun. 27, 2016 to Restriction Requirement dated Mar. 25, 2016", 1 pg.

"U.S. Appl. No. 14/450,110, Restriction Requirement dated Mar. 25, 2016", 7 pgs.

* cited by examiner

DEVICES AND METHODS FOR KNOTLESS MATERIAL FIXATION

This application claims the benefit under 35 U.S.C. 119(e) of the filing date of Provisional U.S. Application Ser. No. 61/861,274, entitled Devices and Systems for Material Fixation, filed on Aug. 1, 2013, which application is herein expressly incorporated herein by reference, in its entirety.

BACKGROUND OF THE INVENTION

There are many suture anchor designs on the market today intended to secure suture, which is passed through soft tissue, to bone. Most pre-loaded suture anchors require tying a knot to secure tissue in place. Knot-tying is time-consuming, prone to technical failure, and may lead to abrasion of the underlying tissue as a result of the mass effect of the suture knot. The preferred method is moving toward using anchors that do not require tying knots in the suture to secure the tissue against bone. Use of a knotless suture anchor construct saves time, requires less technical expertise, and avoids the potential mass effect of a suture knot on the underlying tissue. Also, the knots have been shown to be a common source of anchor failure.

The SwiveLock, by Arthrex, is a two part, screw-in knotless anchor. The tip of the anchor has an eyelet through which the suture legs are loaded. The tip is placed at the bottom of a hole drilled into the bone. The anchor is then screwed into the hole, securing the sutures in the bone hole. The suture ends are passed through the tissue from bottom to top above the anchor. These ends are then loaded into and secured in a knotless anchor implanted off the edge of the tissue. This construct does not provide a knot or other feature to press the tissue down against the bone above the screw-in anchor. A loss of tension in the strands passing between the screw-in and knotless anchors results in reduced compressive force of soft tissue to bone, which may significantly increase the likelihood of gap formation, leading to reduced healing and a compromised repair.

Any screw-in anchor preloaded with suture can be used in this manner. The anchor is placed, the sutures are passed through the tissue, and the free ends are secured in a knotless anchor off the lateral edge of the tissue. However, this construct does not provide compression above the anchor. The only compression on the tissue occurs beneath the suture passing between the anchors.

Smith & Nephew has marketed the KINSA knotless suture anchor. It is a PEEK anchor which is tapped into a pre-drilled hole in the bone. The anchor is preloaded with a loop of suture tied in a one-way sliding knot within the anchor body. The loop is passed through the tissue and the anchor is passed through the loop before inserting it into the bone tunnel. The sliding knot allows the surgeon to pull the free end of suture and tighten the loop through the tissue. This style of anchor is not preferred in the humeral head because of low pull-out forces, the requirement to pass suture prior to installing the anchor, and only 1 suture strand available for loading into a knotless anchor.

SUMMARY OF THE INVENTION

The following disclosure describes the design for a new and novel suture anchor and associated method which is intended to secure tissue to bone. There are many soft-tissue to bone repair procedures, such as rotator cuff, SLAP and Bankart lesion repairs, or reconstruction of labral tissue to the glenoid rim, in which a surgeon needs to secure tissue in close contact with bone. Often the bone surface is roughened, and when soft tissue is directly compressed to a bony surface, improved formation of repair tissue results.

Repair procedures are often performed by implanting an anchor, pre-loaded with suture, into a hole drilled in the bone at the desired anchor location. The two free ends of suture are passed through the soft tissue near the anchor, and the tissue is compressed against the bone surface by tying the suture ends in a knot. In some procedures, such as rotator cuff repair, the remaining free ends are then secured in a knotless anchor placed off the edge of the tissue. This method directly compresses the torn tissue under the knot of pre-loaded anchors and suture limbs of knotless anchors against the underlying bone. It is widely accepted that an ideal soft tissue to bone repair has high fixation strength, minimal gap formation, and sufficient mechanical stability for tendon to bone healing. Additionally, biomechanical studies suggest that a transosseous-equivalent repair improves the ultimate load to failure of the repair and reduces gap formation during cyclic loading when compared with either single- or double-row suture anchor repairs.

The invention described is a simple, threaded suture anchor pre-loaded with suture in a configuration that allows the surgeon to compress tissue against the bone without tying a knot. The knot-tying step is replaced by a simple suture looping step which requires less time and is not prone to errors in knot tying technique.

The suture anchor itself is a screw-in style PEEK anchor, very similar to many pre-loaded anchors currently in use. The suture is loaded into the anchor in a configuration that allows it to create a loop on top of the tissue after it has been passed through the tissue from bottom to top. The limbs are then loaded into a knotless anchor which is implanted off the lateral edge of the tissue. Tensioning of the limbs in the knotless anchor tightens the loop on top of the tissue, providing a fulcrum point of fixation over the pre-loaded suture anchor without the otherwise need for requisite knot tying.

More particularly, there is provided in one aspect of the invention a knotless suture anchor for affixing soft tissue to bone, which comprises an anchor body. The anchor body has external structure for securement to bone and an internal channel, a post within the anchor body at a distal end of the channel, and a loop of suture preloaded into the anchor body and extending distally through the channel, around the post, and then proximally through the channel, so that at least one loop of suture and at least one of either a free end of suture or a second loop of suture extends proximally from a proximal end of the anchor body. In one embodiment, the loop of suture comprises a continuous loop of suture, so that two separate suture loops extend proximally from the proximal end of the anchor body. In another embodiment, the loop of suture preloaded into the anchor body comprises two free ends, so that the two free ends extend proximally from the proximal end of the anchor body, in addition to the at least one loop of suture.

In still another embodiment, the continuous loop of suture is loaded into the anchor body to form three separate loops extending proximally from the proximal end of the anchor body. In some instances, particular in connection with this embodiment, it is advantageous to employ a second post disposed within the anchor body at the distal end of the channel. In this instance, the loop of suture comprises a continuous loop of suture which is disposed around both of the posts and forms three separate loops extending proximally from the proximal end of the suture body.

In some variants of the invention, a sliding knot is tied on a portion of the suture disposed within the anchor body, to create a fixed end or loop of suture extending proximally from the anchor body as well as a free end or loop of suture extending proximally from the anchor body. The fixed end or loop of suture is preferably marked for identification by a surgeon during a repair procedure.

In another aspect of the invention, there is disclosed a method of making an orthopedic repair by fixing a soft tissue graft to bone using a knotless suture anchor comprising an anchor body having external structure for securement to bone and an internal channel, and a loop of suture preloaded into the anchor body so that at least one loop of suture and at least one of either a free end of suture or a second loop of suture extends proximally from a proximal end of the anchor body. The inventive method comprises a step of creating a pilot hole in bone at a desired repair location, inserting the suture anchor into the hole and engaging the anchor with surrounding bone, passing the suture extending from the proximal end of the suture anchor through soft tissue to be attached to the bone, passing the at least one of either a free end of suture or a second loop of suture through the at least one loop of suture, and tensioning the suture to approximate the tissue against the bone. The method then comprises a further step of fully deploying the knotless anchor to secure the suture in place.

The invention, together with additional features and advantages thereof, may best be understood by reference to the following description taken in conjunction with the accompanying illustrative drawing.

DETAILED DESCRIPTION OF THE INVENTION

Referring now more particularly to the drawings, the invention described is a simple threaded suture anchor 10 loaded with suture 12 in a configuration that allows the surgeon to compress tissue against the bone surface without tying a knot.

The anchor 10 comprises an anchor body 13 having external threads 14 to secure it in the bone. The proximal internal diameter (ID) has a square, rectangular, or other non-round cross-section to accept a driver which can transmit torque to screw the anchor into the tunnel. The distal ID has a post around which suture strands can be passed so they may slide within the ID of the anchor.

In order to form a loop on top of the tissue, the suture 12 can be loaded into the anchor 10 in a number of configurations. Three such configurations are shown in FIGS. 1-7.

Figure 1:
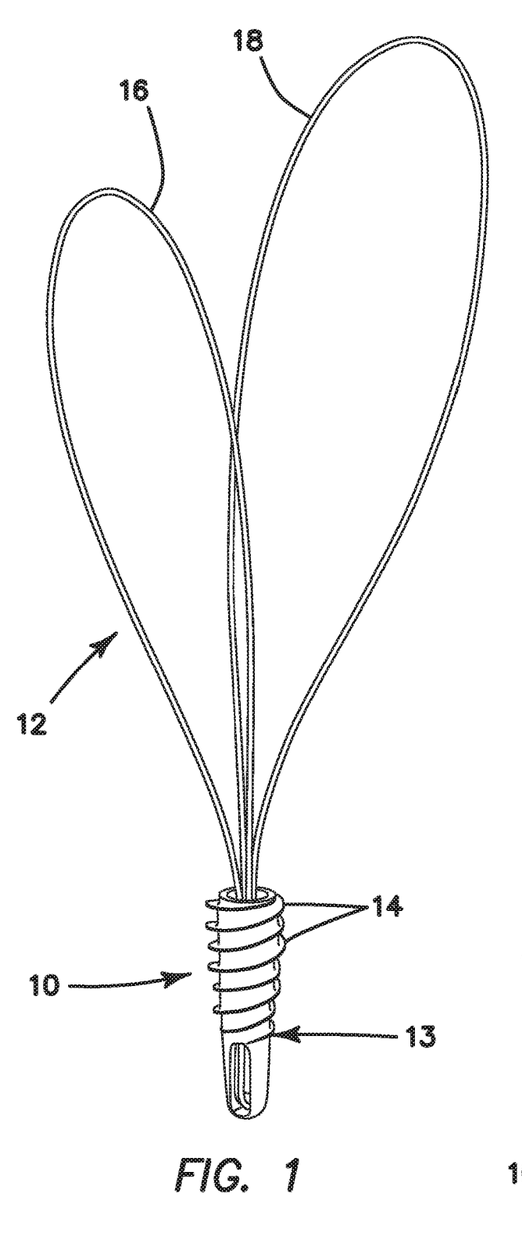
FIG. 1 is a schematic view showing a threaded suture anchor constructed in accordance with the principles of the present invention, with suture loops extending therefrom.
Figure 2:
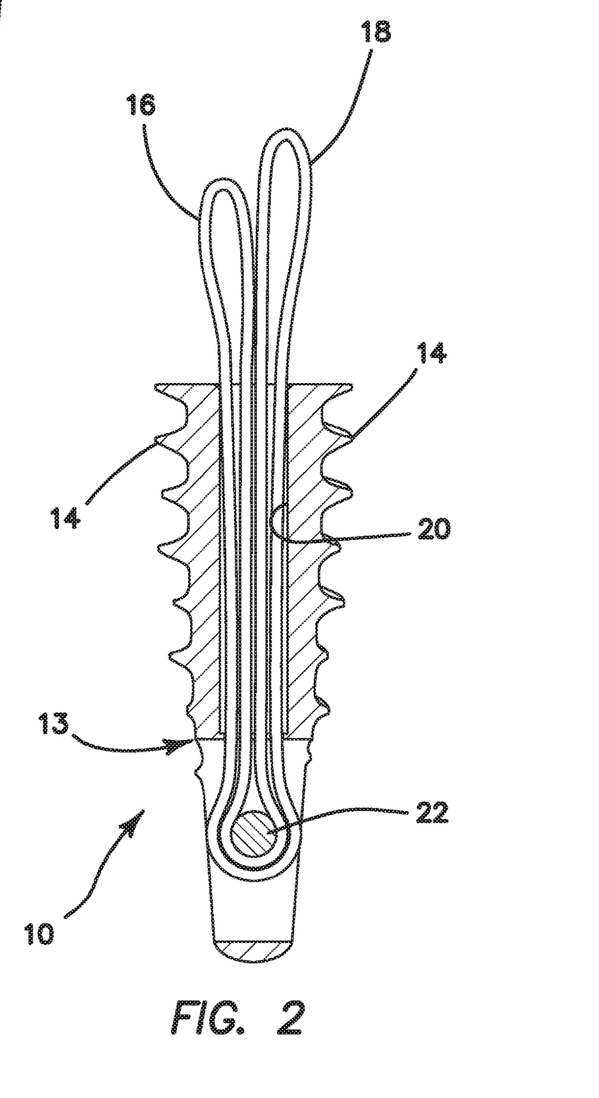
FIG. 2 is a cross-sectional view of the threaded suture anchor of FIG. 1.

FIG. 1 shows a configuration with a first loop 16 and a second loop 18 exiting the anchor body 13. As shown in FIG. 2, a continuous loop of suture passes down the anchor body ID, through a channel 20, around an internal post 22, and back up through the channel 20. The two loops 16, 18 can slide freely around the post 22.

Figures 3, 4:
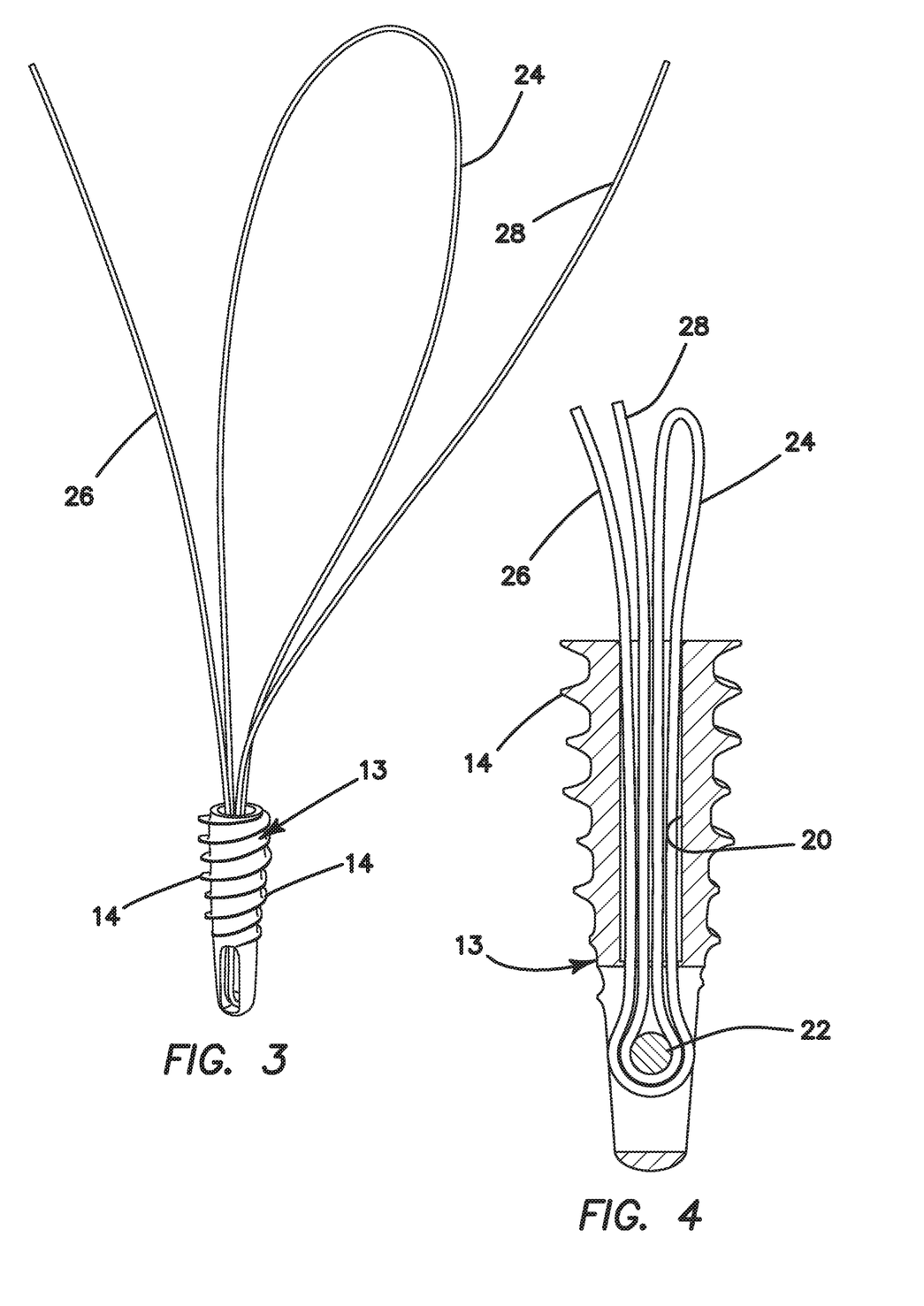
FIG. 3 is a view similar to FIG. 1 showing a modified suture arrangement.
FIG. 4 is a cross-sectional view of the threaded suture anchor of FIG. 3.

FIG. 3 shows a different configuration with a single loop 24 of suture and first and second free ends 26, 28, respectively, of suture exiting the anchor body 13. The two free ends 26, 28 of a single strand of suture pass down the anchor ID through the channel 20, around the post 22, and back up through the channel 20 to form a loop. In this configuration, pulling on a suture free end 26 or 28 tightens one side of the loop. FIG. 4 shows the suture routing inside the anchor.

Figure 5:
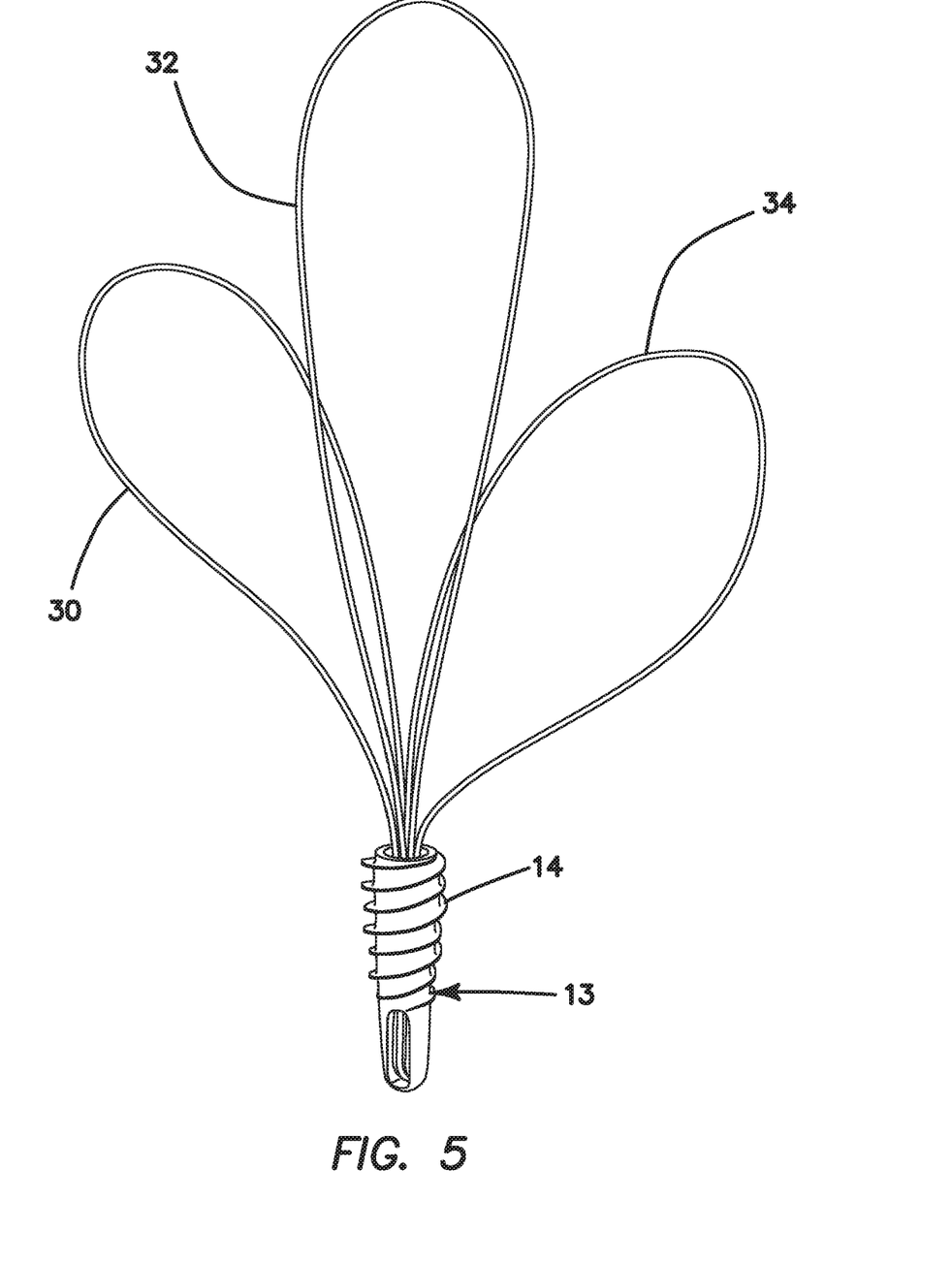
FIG. 5 is a view similar to FIGS. 1 and 3 showing another modified suture arrangement.
Figure 6:
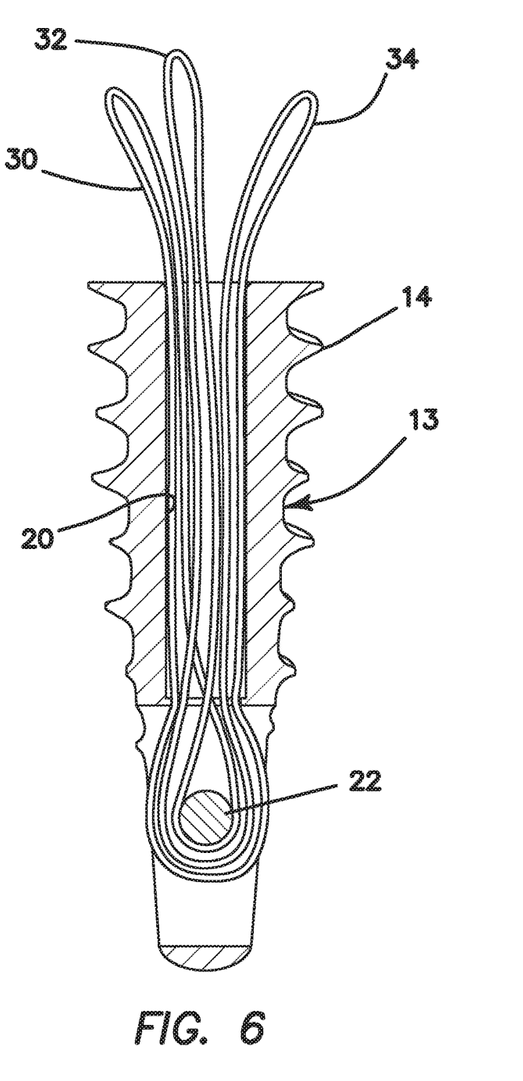
FIG. 6 is a cross-sectional view of the threaded suture anchor of FIG. 5.
Figure 7:
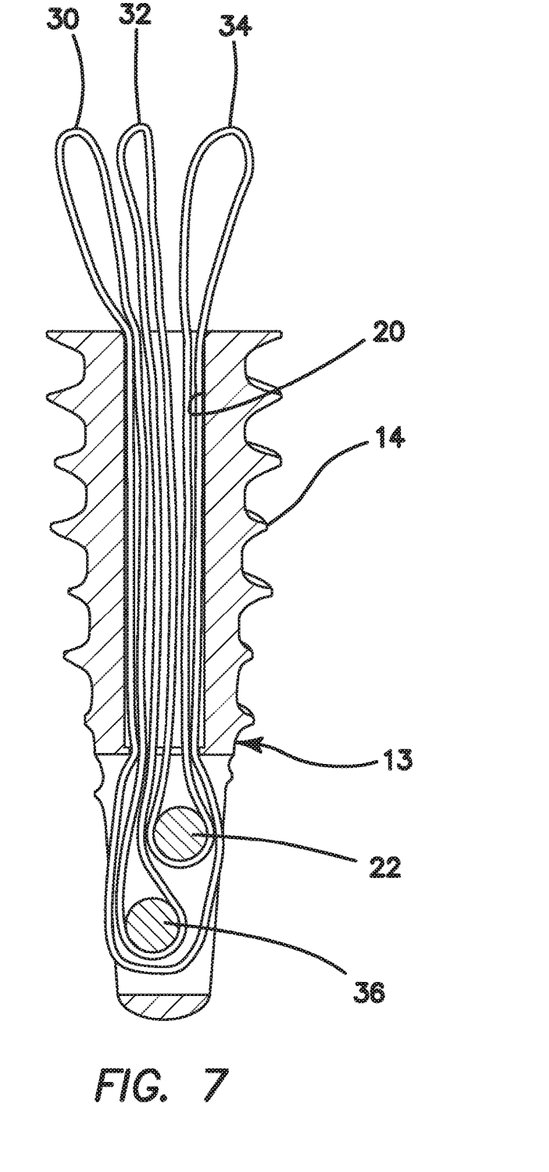
FIG. 7 is a cross-sectional view of a modified embodiment of the threaded suture anchor of FIG. 5.

FIGS. 5 and 6 show an embodiment having a continuous loop of suture loaded into the anchor body 13 to form first, second, and third loops 30, 32, and 34, respectively. It may be desirable to wrap the suture around 2 posts within the anchor to improve suture sliding or suture loading. Such an embodiment is illustrated in FIG. 7, wherein the suture is routed around two posts 22, 36 instead of a single post 22 as shown in FIG. 6.

Figure 8:
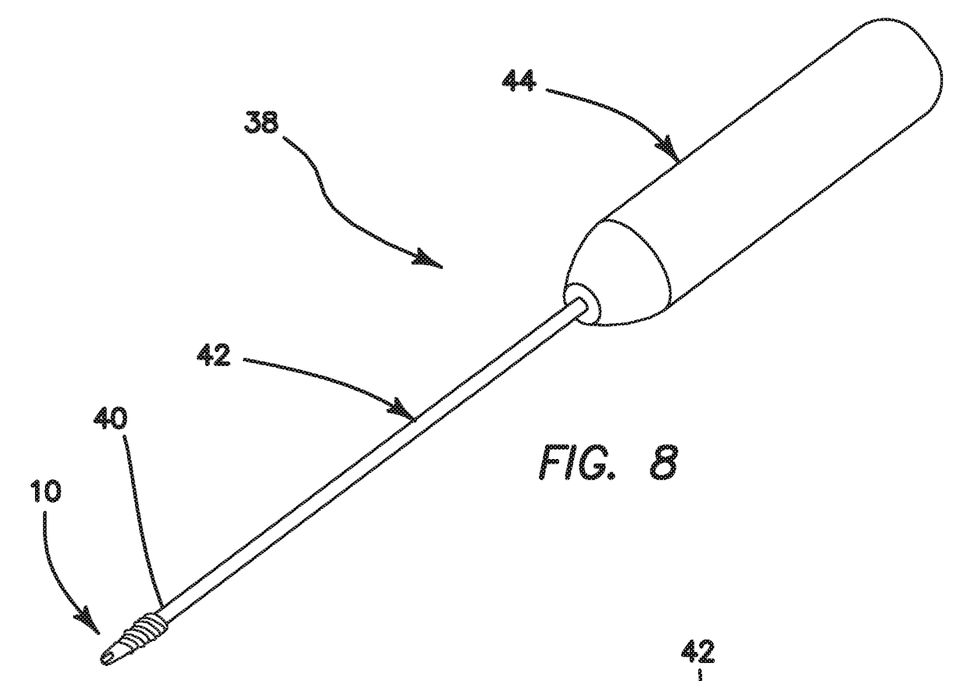
FIG. 8 is an isometric view of an inserter for use with the threaded suture anchors of the present invention.

FIG. 8 illustrates an inserter 38 which may be utilized in connection with the inventive suture anchor system. The anchor 10 is loaded onto a distal end 40 of a driver shaft 42 to allow the surgeon to insert the anchor through a surgical cannula to the location of the repair, by manipulating a handle 44 connected to a proximal end of the shaft 42. The driver also delivers torque to the anchor to screw it into the bone tunnel as well as housing and managing the suture loops and free ends.

Figure 9:
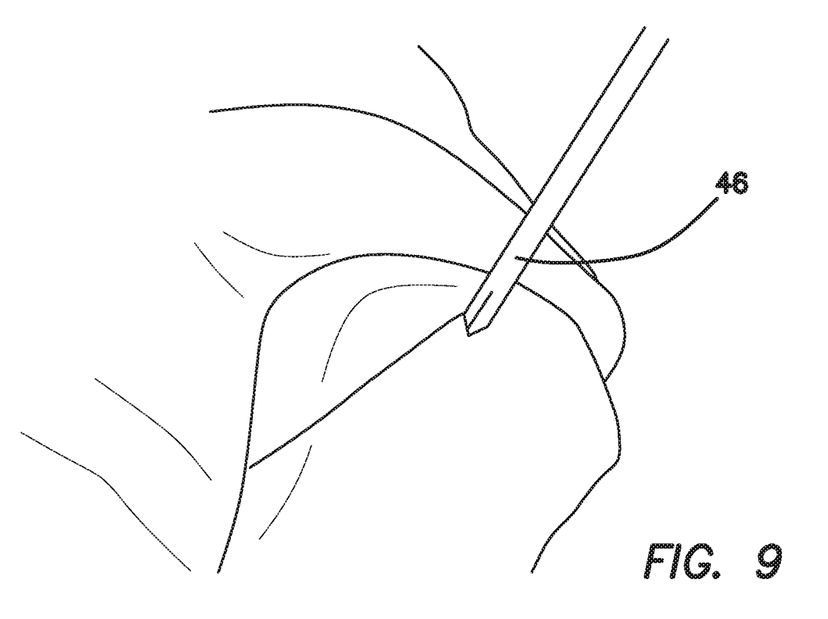
FIG. 9 is a view showing a first step in performing a repair procedure according to the principles of the present invention.
Figure 10:
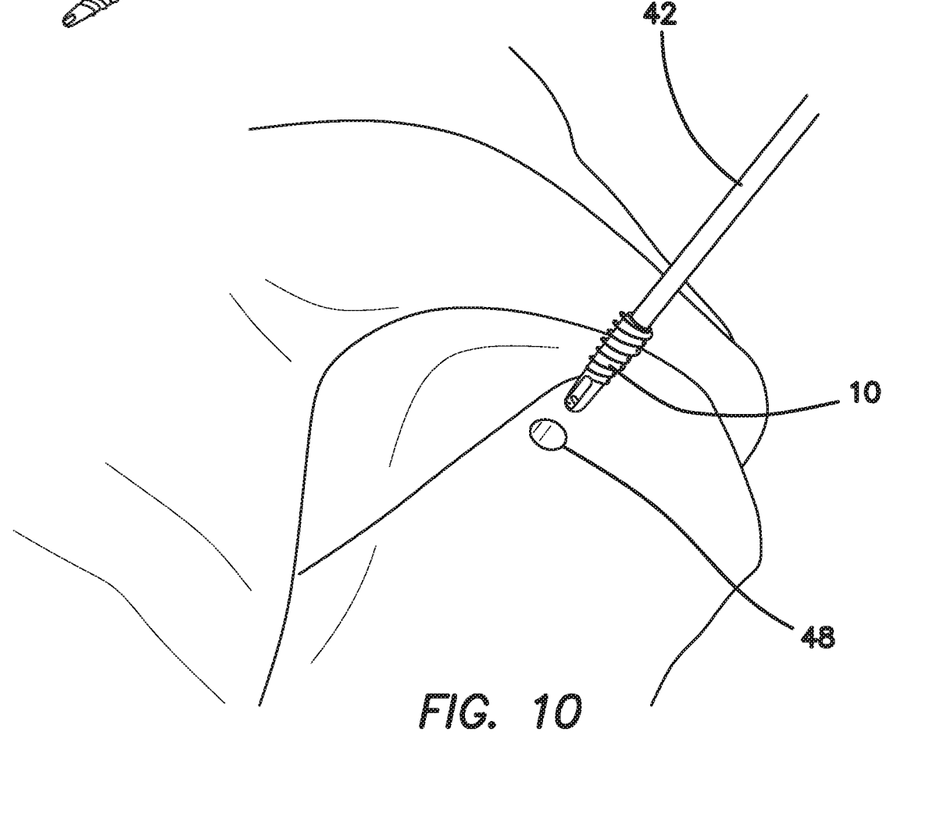
FIG. 10 is a view similar to FIG. 9 showing a next step in the described repair procedure.

A procedure for deploying the anchor 10 of the present invention will now be described, in connection with reference particularly to FIGS. 9-24. First, as shown in FIG. 9, a pilot hole is created in the bone at the desired location using an awl or drill 46. The hole is tapped, if necessary. Then, as shown in FIG. 10, the anchor 10, disposed on the distal end of the driver shaft 42, is screwed into the bone hole 48. The driver, including driver shaft 42, is then removed to expose the suture.

Figure 11:
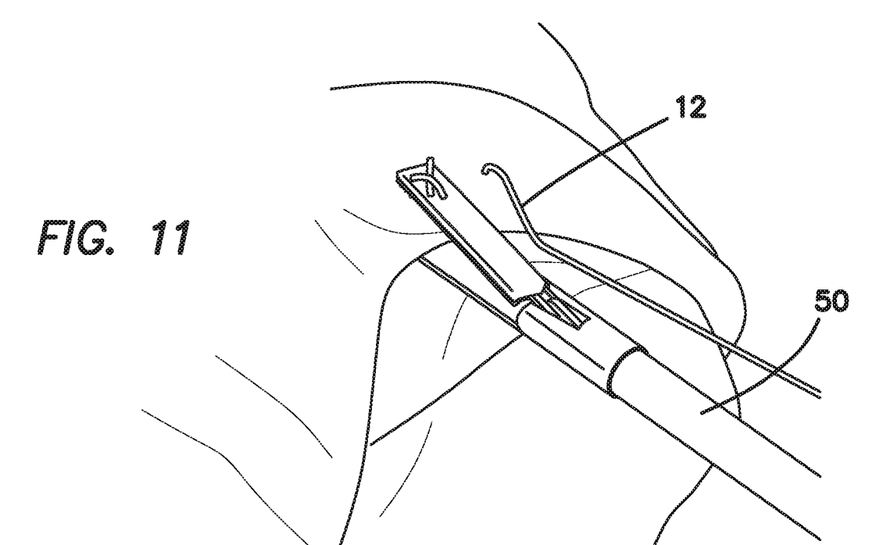
FIG. 11 is a view similar to FIGS. 9 and 10 showing a further step in the described repair procedure.
Figure 12:
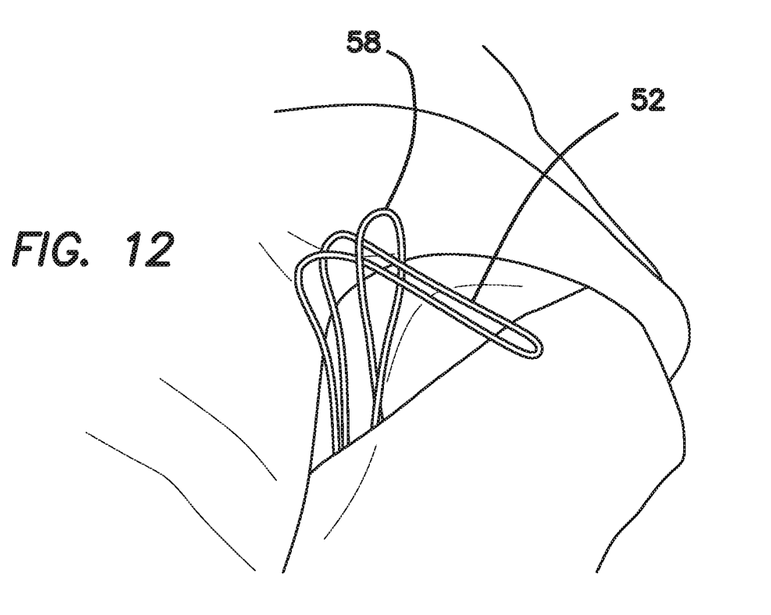
FIG. 12 is a view similar to FIGS. 9-11 showing a further step in the described repair procedure.
Figure 13:
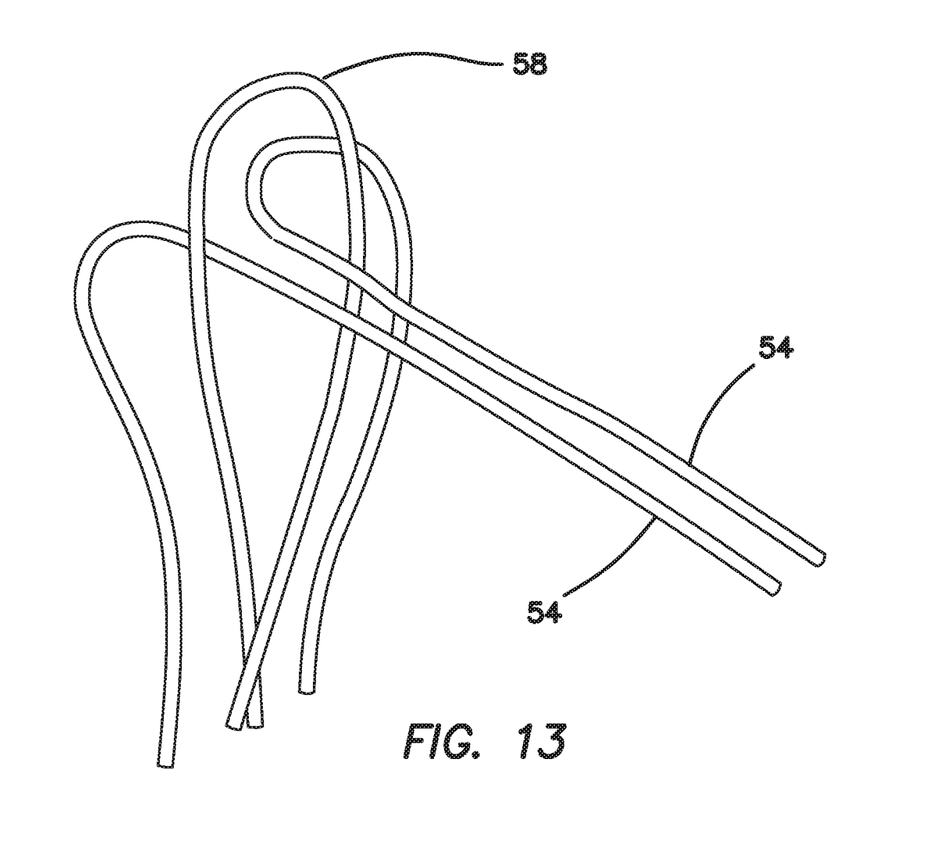
FIG. 13 is a schematic view showing an alternative suture loop arrangement to that shown in FIG. 12.
Figure 14:
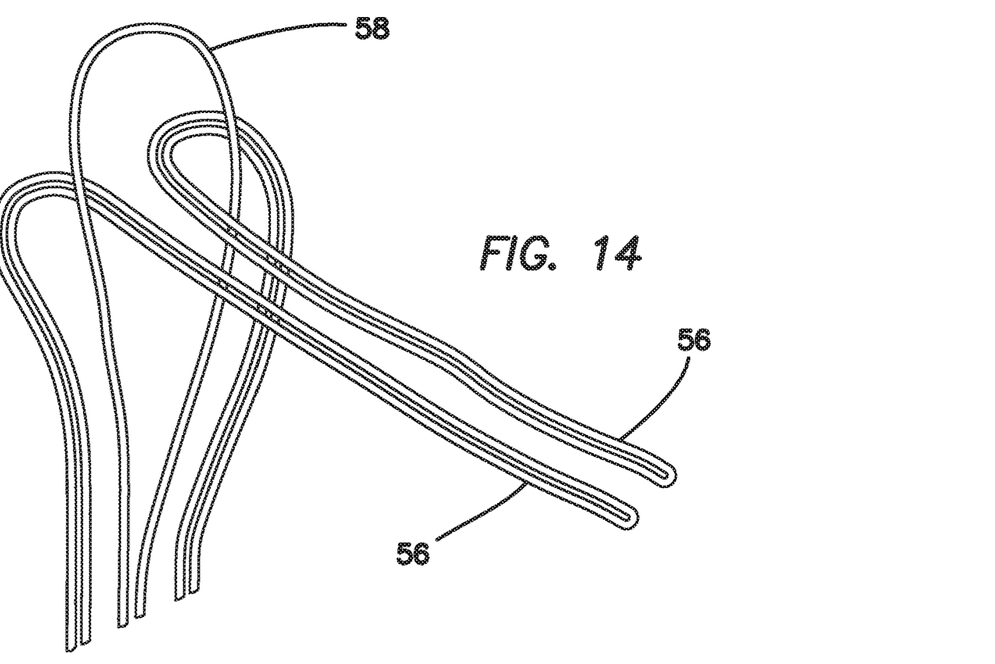
FIG. 14 is a schematic view showing still another alternative suture loop arrangement to those shown in FIGS. 12 and 13.
Figure 15:
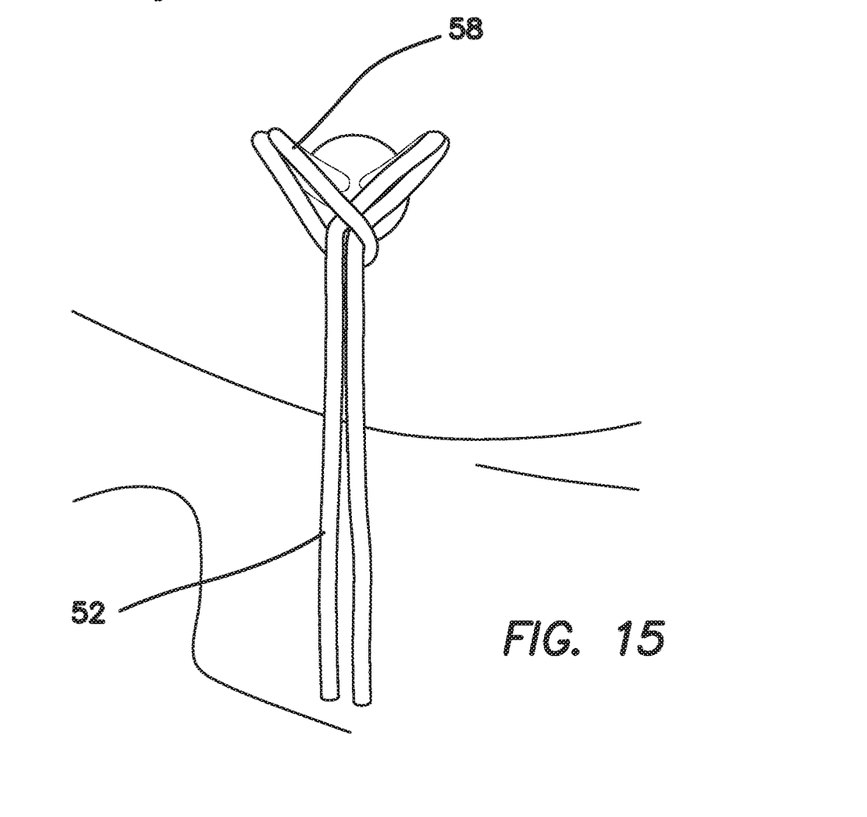
FIG. 15 is a schematic view showing the suture loop pattern of FIG. 1 as it appears externally of the repair site.

As illustrated in FIG. 11, suture 12 is passed through the tissue from bottom to top using an appropriate suture passing instrument 50. Depending on the suture configuration loaded in the anchor, the surgeon will pass two loops, one loop and two suture ends, or three suture loops, as discussed above. FIGS. 12-14 illustrate three possible suture loop arrangements, including passing one loop 52 (FIG. 12), two free ends 54 (FIG. 13), or two loops 56 (FIG. 14) through the center loop 58. This can be done inside or outside the joint space. The loop(s) 52 or 56, or the free ends 54 may be pulled out of the joint space if necessary. The ends are pulled to tighten the center loop 58 above the tissue. The suture loops 52 or 56 or the free ends 54 are loaded into a knotless anchor 10. The suture limbs are tensioned in the knotless anchor to tighten the center loop 58 and approximate the tissue against the bone. The knotless anchor 10 is then fully deployed to secure the suture in place.

The resulting loop pattern on top of the tissue depends on the loading configuration of the anchor. An anchor loaded with a continuous loop of suture, as shown in FIG. 1, results in the loop pattern shown in FIG. 15. This configuration requires only two passes of suture through the tissue. The loop can be secured into a knotless anchor or cut to form two free ends. These two free ends can then be loaded into two knotless anchors.

Figure 16:
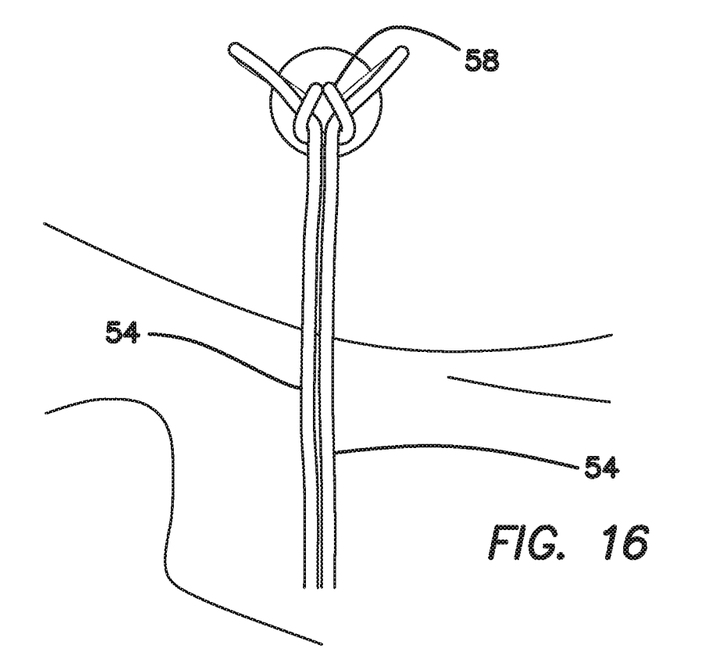
FIG. 16 is a schematic view similar to FIG. 15 showing the suture loop pattern of FIG. 3 as it appears externally of the repair site.

An anchor loaded with one strand of suture forming a loop and two free ends, as shown in FIG. 3, results in a loop pattern as shown in FIG. 16. This pattern is more symmetric than the pattern shown in FIG. 15 and allows for a more intuitive use with a sliding knot (see design variations below). The two free ends can be secured into one or two knotless anchors.

Figure 17:
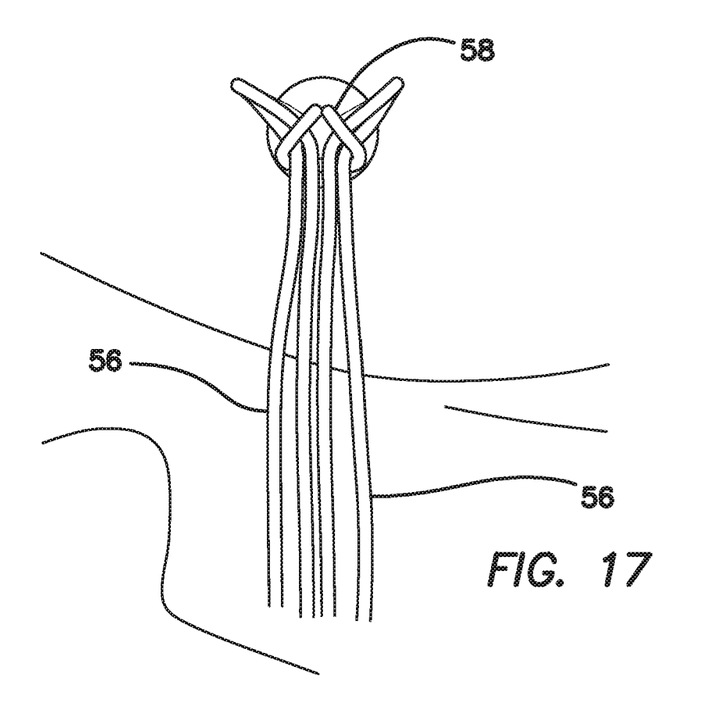
FIG. 17 is a schematic view similar to FIGS. 15 and 16 showing the suture loop pattern of FIG. 5 as it appears externally of the repair site.

An anchor loaded with 3 loops outside the anchor, as shown in FIG. 5, results in a loop pattern as shown in FIG. 17. This pattern results in two loops exiting the anchor (4 strands), resulting in more suture surface area compressing tissue. The two loops can be secured in one or two knotless anchors.

Figures 18, 19:
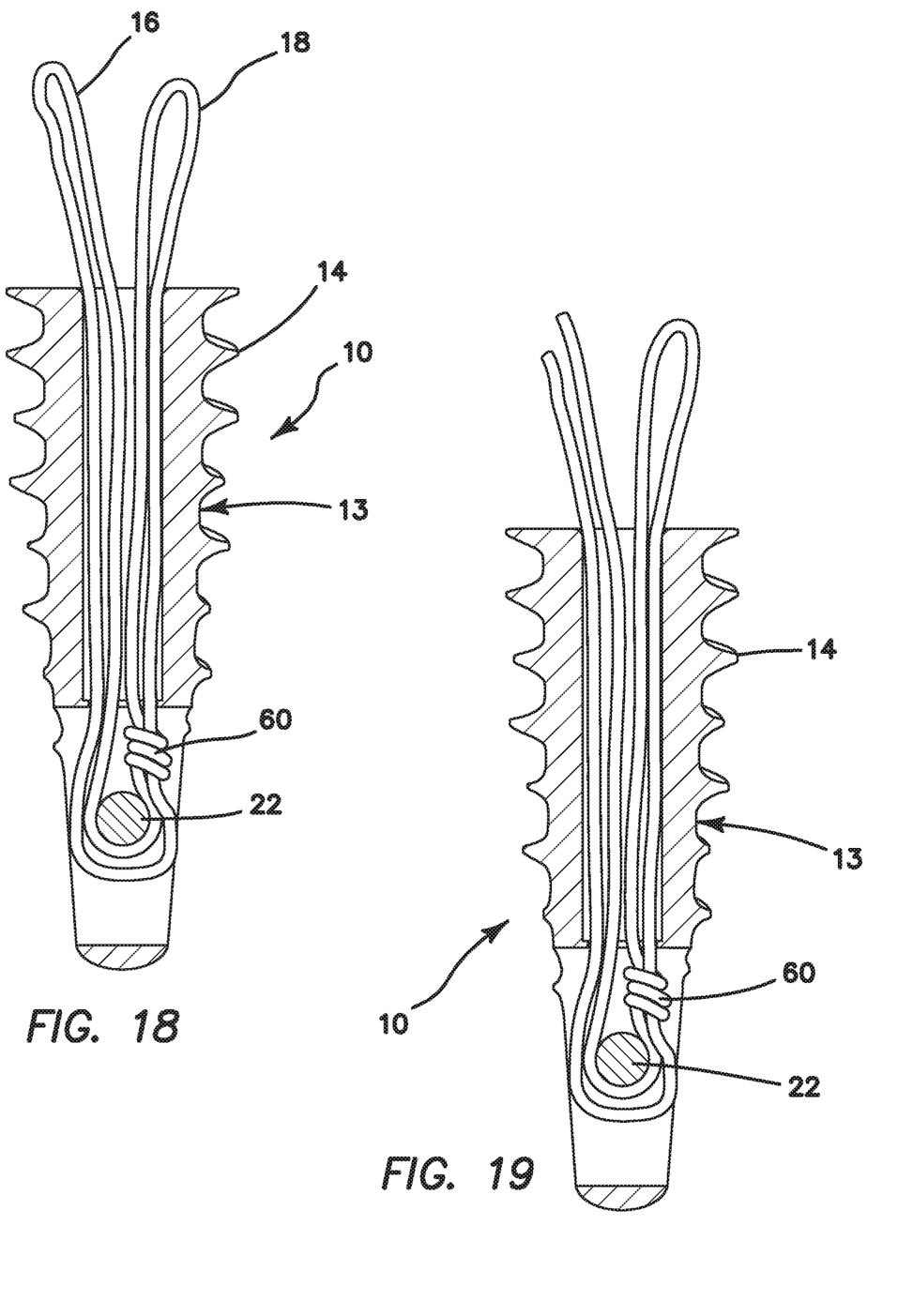
FIG. 18 is a cross-sectional view showing a particular suture routing arrangement incorporating the use of a sliding knot.
FIG. 19 is a cross-sectional view similar to FIG. 18 showing another particular suture routing arrangement incorporating the use of a sliding knot.
Figures 20, 21:
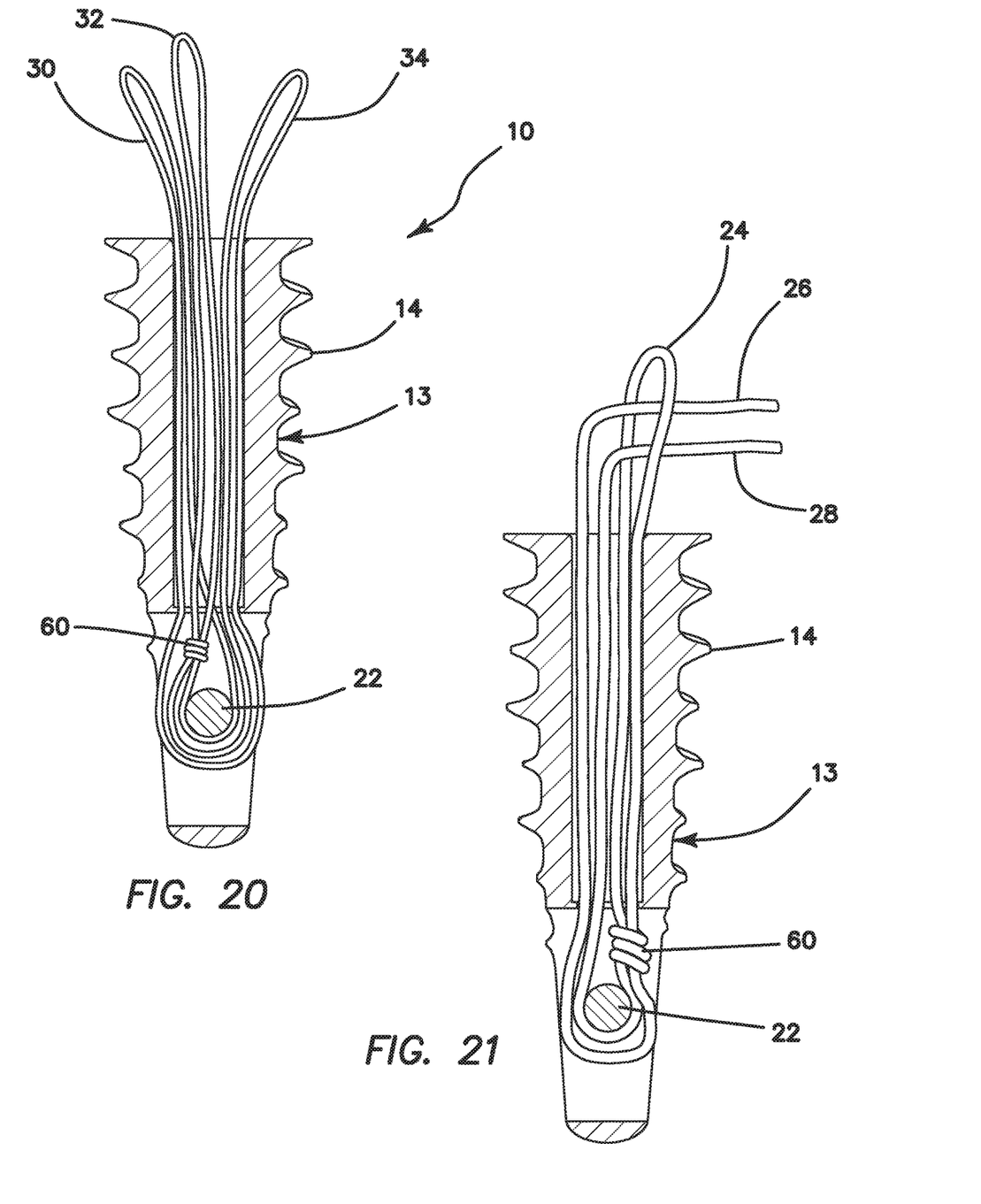
FIG. 20 is a cross-sectional view similar to FIGS. 18 and 19 showing another particular suture routing arrangement incorporating the use of a sliding knot.
FIG. 21 is a cross-sectional view of the suture anchor of the invention showing an arrangement for marking which free end of the suture loop is fixed and which one should be pulled to tension the loop.

A design variation on the concept described above incorporates a sliding knot 60 within the anchor. This knot is tied with the suture strands forming the center loop. A preferred knot for this application is a ratchet knot—one which preferentially slides in only one direction. This knot, such as a Duncan Loop, Tennessee slider, or other sliding knot, allows the loop to tighten but not loosen easily. This provides extra security and maintains downward pressure on the tissue in the event that tension is lost in the free ends or loop(s). It also allows the surgeon to reduce the size of the center loop independently of the tension placed on the limbs to provide more compression above the anchor if desired. In addition, the surgeon may want to tighten the center loop prior to loading the free ends in the knotless anchor to check suture placement or preview the final repair. The suture routing for this design variation is shown in FIGS. 18-20.

With this design variation, the procedure for tightening the loop changes slightly. The presence of the sliding knot creates a post, or non-moving suture end. Once the sutures are passed through the tissue and the ends passed through the loop, the surgeon pulls on the tightening limb only. This tightens the loop around the sutures passing through it and approximates the tissue against the bone.

The knot 60 can be incorporated into all of the loading configurations shown in FIGS. 1-7. However, the configuration shown in FIG. 3 is a particularly desirable one—the knot is easily tied (during loading of the suture into the anchor) and the surgeon has one fixed end and one free end for tightening the suture loop on top of the tissue. Desirable embodiments have the fixed end 26 clearly marked so the surgeon can easily tell which suture to pull for tensioning (see FIG. 21).

Figures 22, 23:
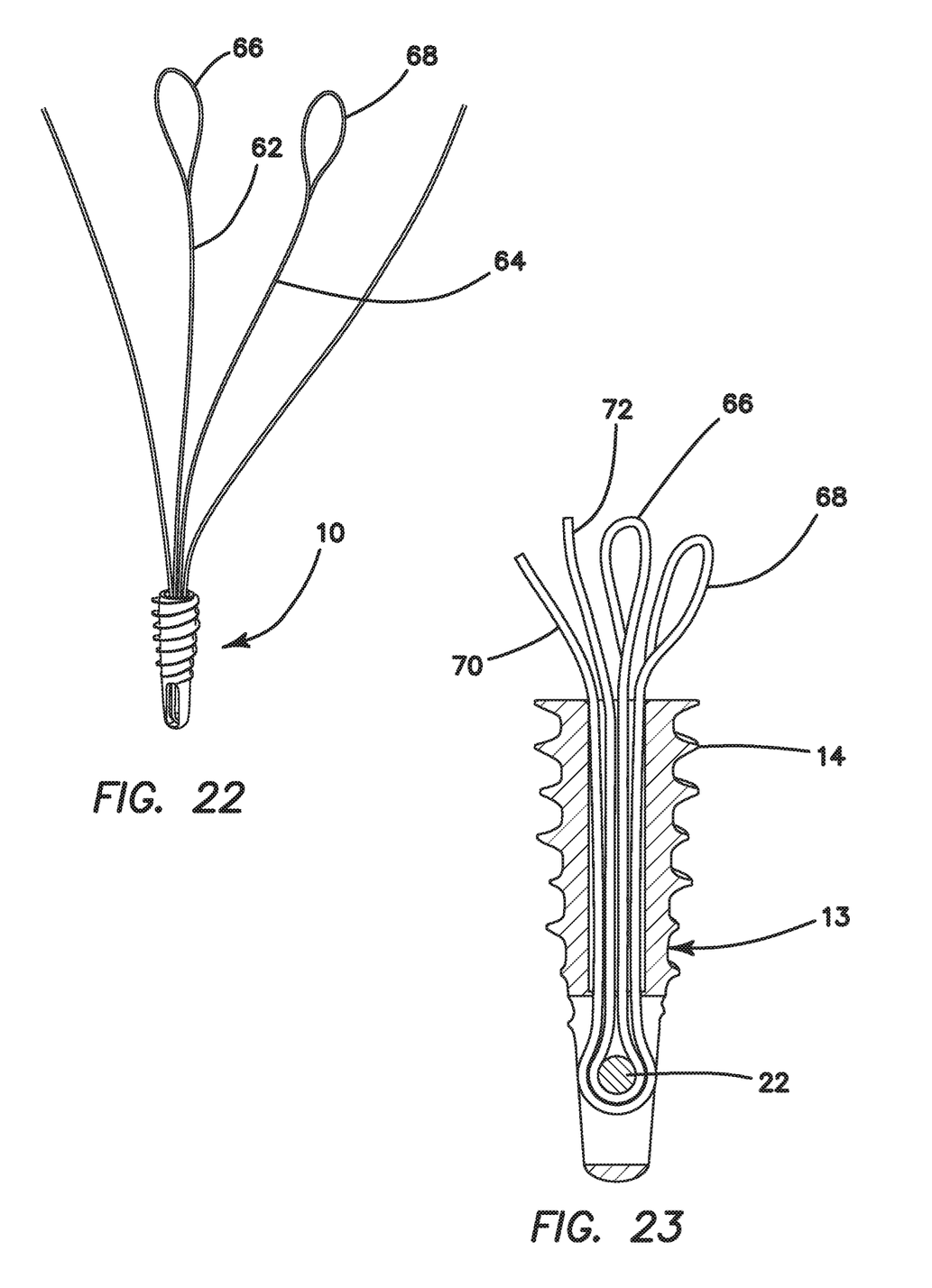
FIG. 22 is a schematic view illustrating a suture loop arrangement having first and second looped ends.
FIG. 23 is a cross-sectional view of the suture anchor showing the routing within the anchor for the suture loop arrangement of FIG. 22.
Figure 24:
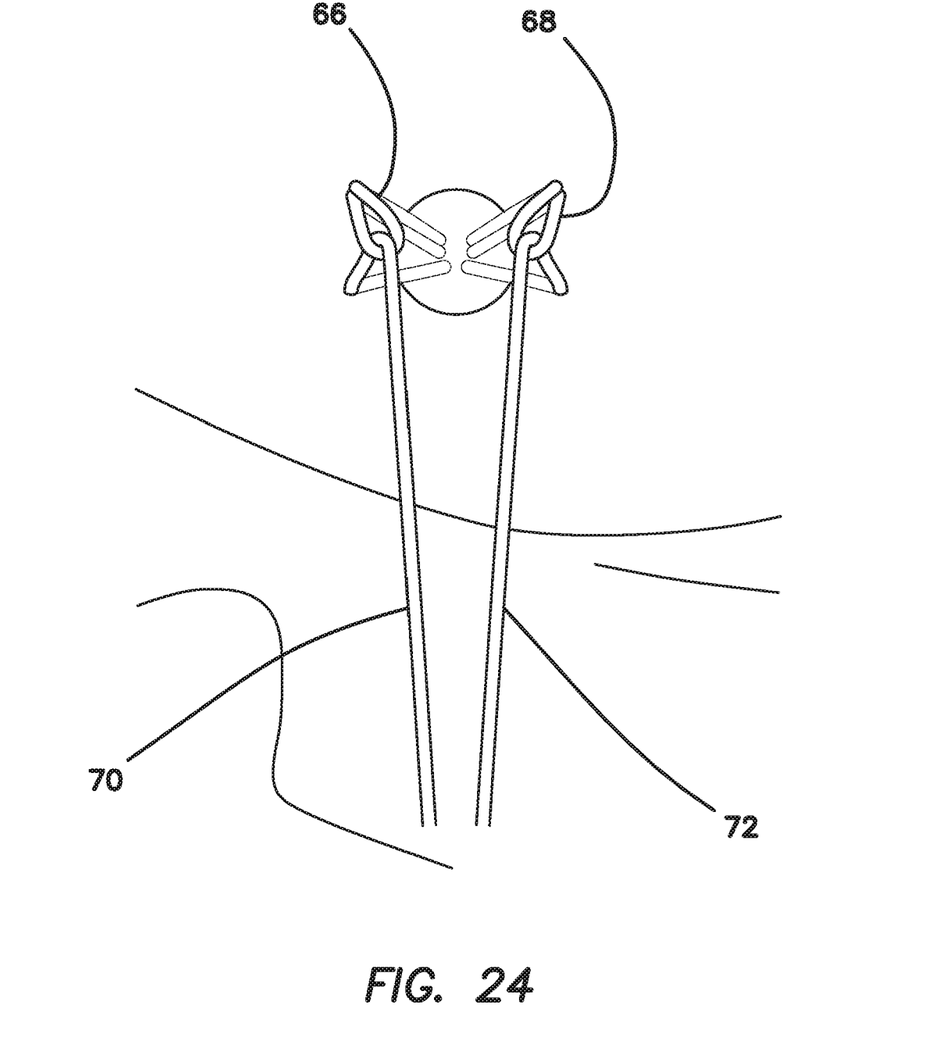
FIG. 24 is a schematic view showing the loop pattern resulting from the suture loop arrangement illustrated in FIGS. 22 and 23.

Another design variation consists of the anchor loaded with first and second strands of suture 62, 64, respectively, with first and second looped ends 66, 68, respectively (see FIG. 22), as well as first and second free ends 70, 72, respectively. The suture routing inside the anchor is shown in FIG. 23 with the resulting loop pattern shown in FIG. 24. This configuration requires the surgeon to pass four sutures through the tissue, but can provide a large footprint of compression above the anchor. This variation does not allow incorporation of the sliding knot (see FIGS. 18-21).

Accordingly, although exemplary embodiments of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of making an orthopedic repair by fixing soft tissue to bone using a suture anchor comprising an anchor body having external structure for securement to bone and an internal channel, and a loop of suture preloaded into the anchor body so that at least one loop of suture and at least one of either a free end of suture or a second loop of suture extends proximally from a proximal end of the anchor body and so that a sliding knot is formed within the anchor body, comprising:

creating a pilot hole in bone at a desired repair location;

loading the suture anchor onto a distal end of a driver shaft of an inserter such that the inserter houses and manages the at least one loop of suture and the at least one of either a free end of suture or a second loop of suture;

inserting the suture anchor into the hole and engaging the anchor with surrounding bone;

removing the driver shaft from engagement with the suture anchor to expose the at least one loop of suture and the at least one of either a free end of suture or a second loop of suture;

passing the suture extending from the proximal end of the suture anchor through the soft tissue to be attached to the bone;

passing the at least one of either a free end of suture or a second loop of suture through the at least one loop of suture; and tensioning the suture to approximate the soft tissue against the bone.

2. The method as recited in claim 1, and further comprising a step of fully deploying the anchor to secure the suture in place.

3. The method as recited in claim 1, wherein the external structure of the anchor body comprises one or more external threads.

4. The method as recited in claim 1, wherein the loop of suture comprises a continuous loop of suture.

5. The method as recited in claim 1, further comprising manipulating a handle connected to a proximal end of the driver shaft of the inserter to deliver torque for engaging the suture anchor with the surrounding bone.

6. A method of making an orthopedic repair by fixing soft tissue to bone, comprising:

creating a pilot hole in bone at a desired repair location;

loading a knotless suture anchor onto a distal end of an inserter, the suture anchor including an anchor body having a closed distal end, external structure for securement of the anchor body to the surrounding bone, an internal channel extending partially through the anchor body, and a continuous loop of suture preloaded into the anchor body such that the continuous loop of suture creates two separate loops that extend from an opening in a proximal end of the anchor body including a first loop of suture and a second loop of suture, wherein the inserter houses the suture extending from the opening in the proximal end of the anchor body when the suture anchor is loaded onto the inserter;

inserting the suture anchor into the hole and engaging the suture anchor with surrounding bone;

disengaging the inserter from the suture anchor to expose the suture extending from the opening in the proximal end of the anchor body;

passing the first loop of suture extending from the opening in the proximal end of the anchor body through the soft tissue to be attached to the bone;

passing the second loop of suture through the first loop of suture; and tensioning the suture to approximate the soft tissue against the bone.

7. The method as recited in claim 6, further comprising fully deploying the suture anchor to secure the suture in place.

8. The method as recited in claim 6, wherein engaging the suture anchor with the surrounding bone comprises threadedly engaging the suture anchor with the surrounding bone.

9. The method as recited in claim 6, wherein the suture extends around a post disposed within the anchor body at a distal end of the internal channel.

10. The method as recited in claim 6, wherein the continuous loop of suture further includes a third loop of suture extending proximally from the proximal end of the anchor body.

11. The method as recited in claim 6, further comprising manipulating a handle of the inserter to deliver torque for engaging the suture anchor with the surrounding bone.

12. A method of making an orthopedic repair by fixing soft tissue to bone, comprising:

creating a pilot hole in bone at a desired repair location;

inserting a suture anchor into the hole and engaging the anchor with surrounding bone, the suture anchor including an anchor body extending from an open proximal end to a closed distal end, an internal channel disposed within the anchor body and extending from the open proximal end toward the closed distal end, and a continuous loop of suture preloaded into the anchor body such that the continuous loop of suture extends distally around a post disposed within the anchor body at a distal end of the internal channel and then proximally through the internal channel such that the continuous loop of suture creates three separate loops that extend from the open proximal end of the anchor body including a first loop of suture, a second loop of suture, and a third loop of suture;

passing the first loop of suture extending from the open proximal end of the anchor body through the soft tissue to be attached to the bone; and passing the second loop of suture through the first loop of suture.

13. The method as recited in claim 12, further comprising tensioning the suture to approximate the soft tissue against the bone.

14. The method as recited in claim 12, wherein the anchor body includes external structure for securement to the surrounding bone.

15. The method as recited in claim 14, wherein the external structure comprises one or more threads.

* * * * *